US00PP24875P3

(12) United States Plant Patent
Wheeler et al.

(10) Patent No.: US PP24,875 P3
(45) Date of Patent: Sep. 16, 2014

(54) BLUEBERRY PLANT NAMED 'BB05-185GA'

(50) Latin Name: *Vaccinium corymbosum*
Varietal Denomination: BB05-185GA

(71) Applicant: Berry Blue, LLC, Grand Junction, MI (US)

(72) Inventors: Edmund J. Wheeler, Holland, MI (US); James F. Hancock, East Lansing, MI (US)

(73) Assignee: Berry Blue, LLC, Grand Junction, MI (US)

( * ) Notice: Subject to any disclaimer, the term of this patent is extended or adjusted under 35 U.S.C. 154(b) by 77 days.

(21) Appl. No.: 13/651,273

(22) Filed: Oct. 12, 2012

(65) Prior Publication Data

US 2014/0109268 P1 Apr. 17, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP9,834 | P | 3/1997 | Lyrene |
| PP10,675 | P | 11/1998 | Lyrene |
| PP11,807 | P2 | 3/2001 | Lyrene |
| PP11,829 | P2 | 4/2001 | Lyrene |
| PP12,165 | P2 | 10/2001 | Lyrene |
| PP15,103 | P3 | 8/2004 | Hancock |
| PP15,146 | P3 | 9/2004 | Hancock |
| PP16,333 | P3 | 3/2006 | Lyrene |
| PP16,404 | P3 | 4/2006 | Lyrene |
| PP18,138 | P3 | 10/2007 | Nesmith |
| PP19,503 | P3 | 11/2008 | Lyrene |
| PP20,027 | P3 | 5/2009 | Lyrene |
| PP21,881 | P3 | 4/2011 | Patel |
| PP22,692 | P3 | 5/2012 | Nesmith |
| PP22,778 | P3 | 6/2012 | Wright et al. |

*Primary Examiner* — Annette Para
(74) *Attorney, Agent, or Firm* — Graybeal Jackson LLP

(57) ABSTRACT

A new and distinct cultivar of blueberry plant named 'BB05-185GA' as described and shown herein. 'BB05-185GA' is a new and distinct low chill tetraploid Southern highbush blueberry (*Vaccinium*) variety of complex ancestry, based largely on *V. corymbosum* and with over 13% *V. darrowii* and small contributions of *V. angustifolium, V. tenellum*, and *V. ashei*. It is a productive mid-late season variety that ripens between Star, a widely planted mid-season highbush variety, and Climax, an early season rabbiteye variety. It is characterized as having a very large fruit with a very small and dry picking scar, light blue color, very firm with outstanding fruit quality and flavor for fresh market. In part 'BB05-185GA' provides outstanding fruit quality and flavor, its harvest season fills a void between highbush and rabbiteye seasons and it has good machine harvest potential.

5 Drawing Sheets

1

BACKGROUND AND SUMMARY

Blueberries are a well-known fruit enjoyed by many throughout the world. One example of an existing, patented blueberry variety is Star, U.S. Plant Pat. No. 10,675. Another example of an existing, patented blueberry variety is Rebel, U.S. Plant Pat. No. 18,138.

Compared to Star, the present cultivar, 'BB05-185GA', has a fruit color that is much lighter in color. The chill requirement for 'BB05-185GA' is slightly more (500 hrs vs. 400 hrs). Fruit maturity is about 7 days later than Star. Fruit size is much larger and consistent in sizing. New leaf growth is reddish in color.

Compared to Rebel, 'BB05-185GA' has a more upright bush shape. The chill requirement for 'BB05-185GA' is more than Rebel (500 vs. 300). Fruit maturity is later than Rebel by 10-14 days. Fruit is lighter blue color, firmer and with very high sweetness as compared to Rebel. New leaf growth is reddish in color.

The present cultivar, 'BB05-185GA', provides one or more advantages compared to these and/or other blueberry varieties.

2

BRIEF DESCRIPTION OF THE PHOTOGRAPHS

DETAILED DESCRIPTION

Figure 1:
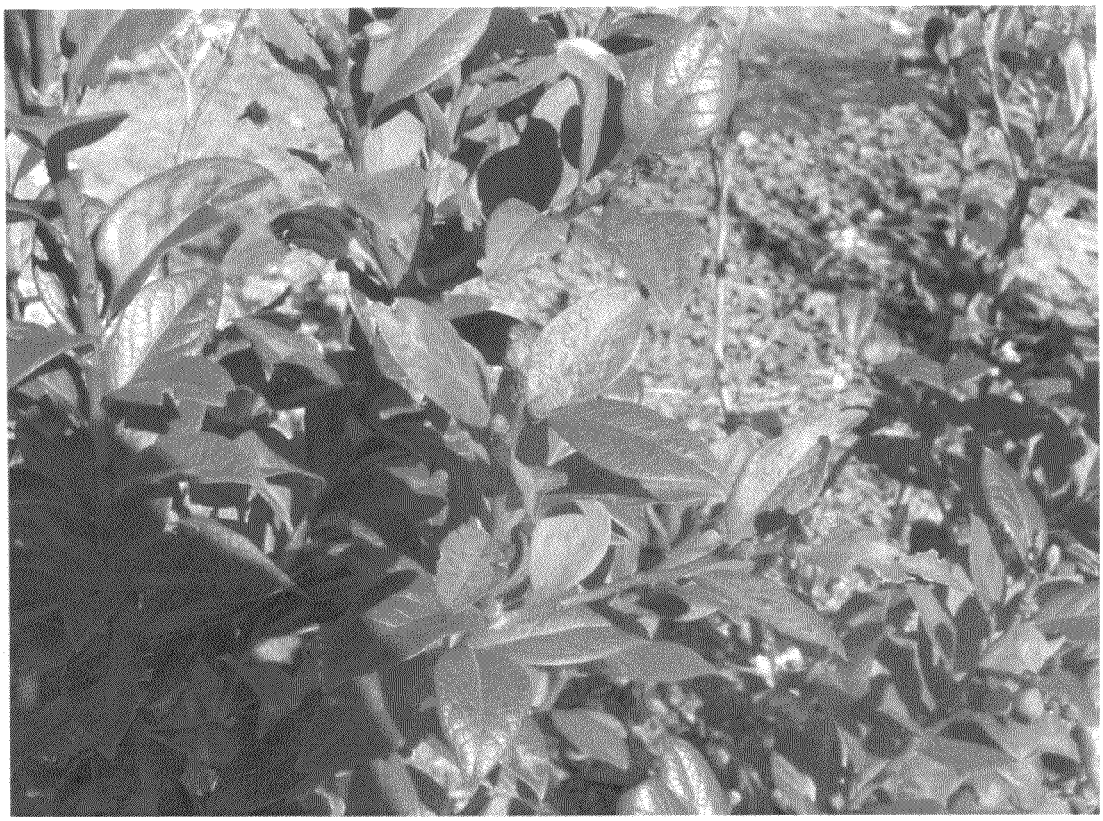
FIG. 1 is a photograph taken in March 2012 of the Blueberry cultivar 'BB05-185GA', showing evergreen leafing with reddish color of older and younger leaves during cool weather, leaf shape, fruiting wood color, leaf arrangement, petiole length and color, venation of leaves.
Figure 2:
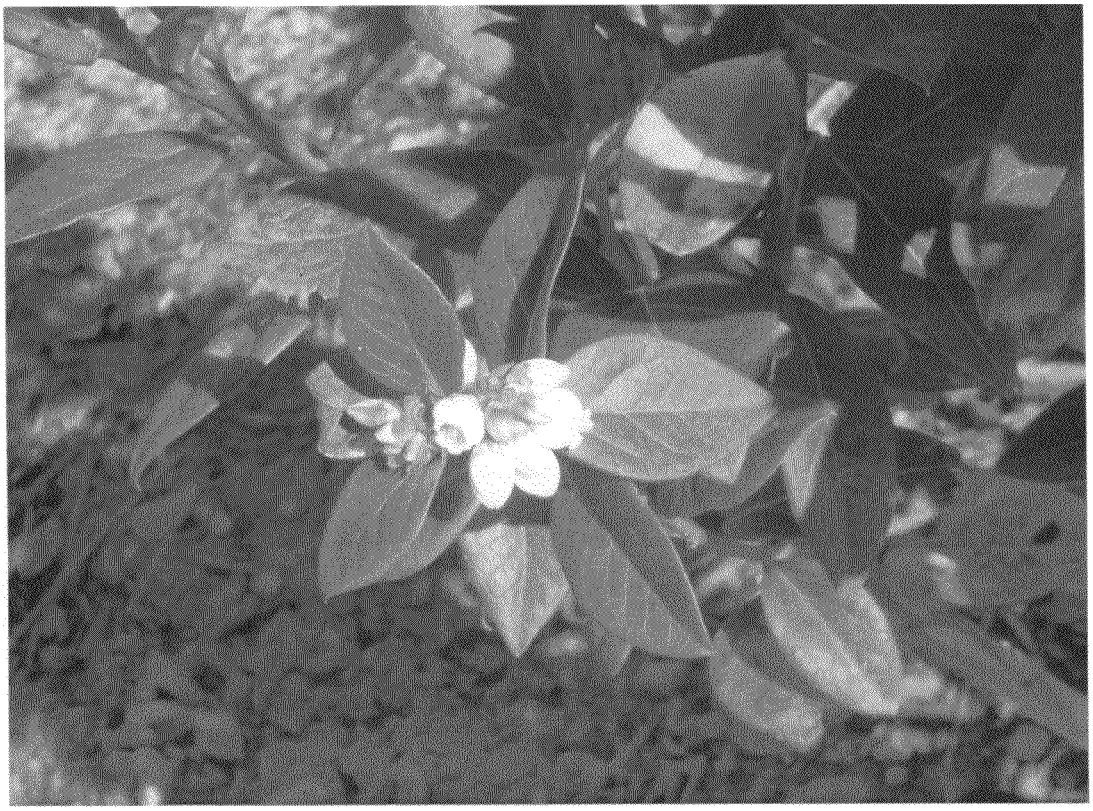
FIG. 2 is a close-up photograph taken in February 2012 of the Blueberry cultivar 'BB05-185GA' showing the color and shape of opened flowers, as well as unopened flowers, the reddish coloration of leaves, and flower number per cluster.
Figure 3:
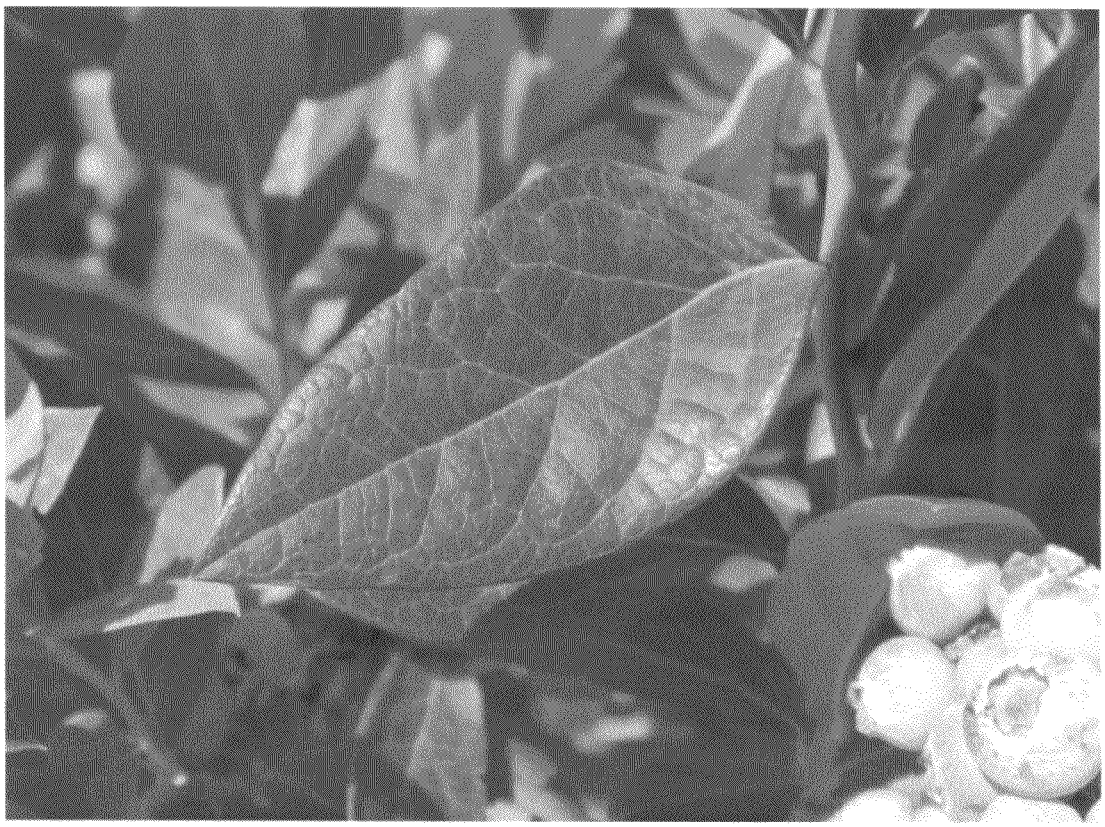
FIG. 3 is a close-up photograph taken in April-May 2012 of the Blueberry cultivar 'BB05-185GA', showing mature leaves showing shape, venation, color, leaf margins, petiole length and color, as well as a cluster of unripe berries with density and color, and the color of new fruiting wood.
Figure 4:
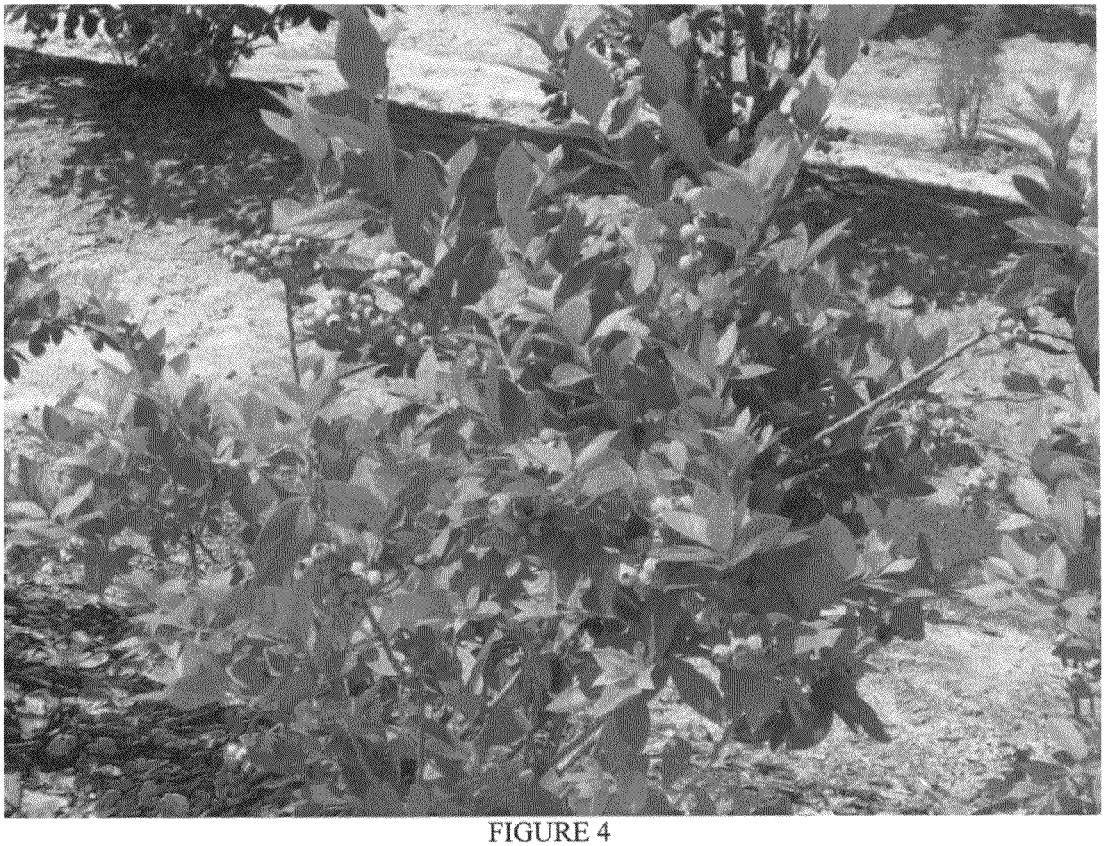
FIG. 4 is a photograph taken in May 2012 of the Blueberry cultivar 'BB05-185GA', showing bush shape, as well as leafing, fruit presentation, cluster density, and ripe and unripe fruit.
Figure 5:
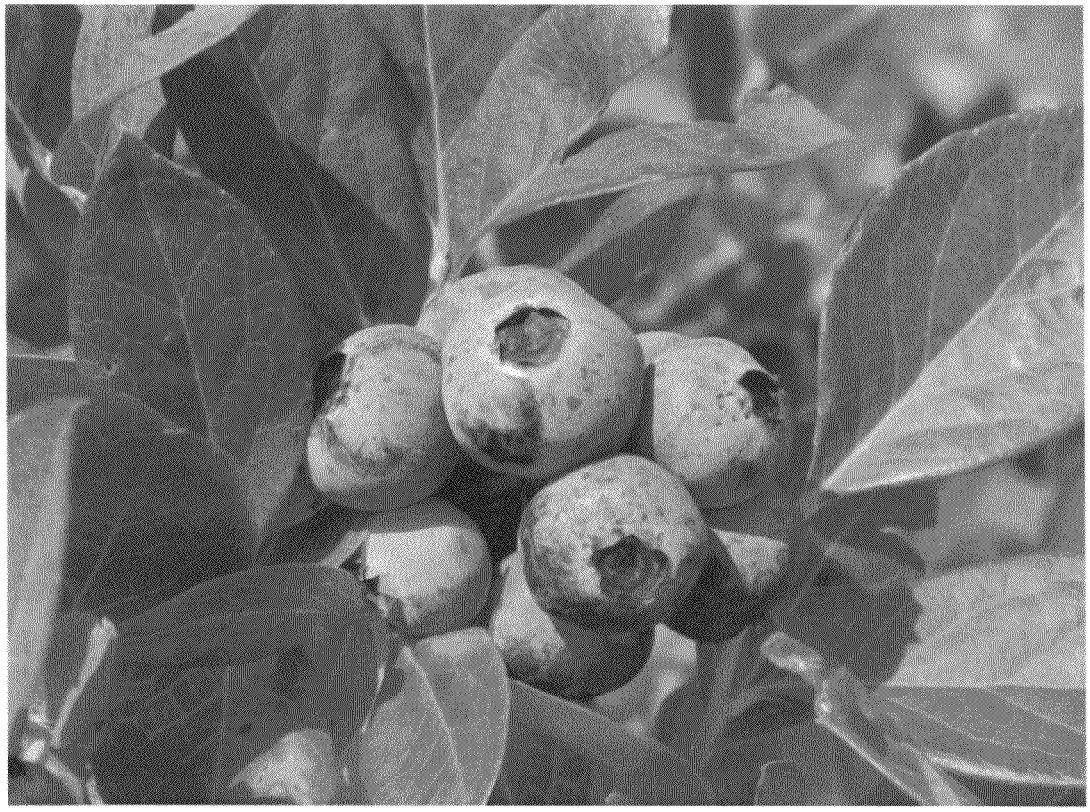
FIG. 5 is a close-up photograph taken in May 2012 of the Blueberry cultivar 'BB05-185GA', showing a fruit cluster with ripe berries. This also shows cluster density, ripe color, shape of fruit, calyx size and shape, leaf shape, and petiole length and color.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely from specimen plants grown near Manor, Ga. Data were obtained on a plant that was 3 years old.

Cultivar name: 'BB05-185GA'.

Classification:

*Family*.—Ericaceae.

*Botanical name*.—*Vaccinium corymbosum*.

*Common name*.—Blueberry.

Parentage:

*Female parent*.—Cooper (unpatented) (G180 unpatented×US75 unpatented). U.S. Plant Pat. No.: none. Compared to Cooper, 'BB05-185GA' has a higher chill requirement (400 vs. 500). Cooper has much smaller and darker blue colored berries and Cooper ripens 10 days before 'BB05-185GA'. Cooper has medium upright habit while the habit for 'BB05-185GA' is upright. Cooper blooms 5-10 days later than 'BB05-185GA'.

*Male parent*.—Name: Draper (Duke unpatented×G751 unpatented). U.S. Plant Pat. No.: 15,103. Compared to Draper, 'BB05-185GA' has a much lower chill requirement (800 vs. 500); 'BB05-185GA' is adapted to a lower chill production area, while Draper is not. The bush shape of 'BB05-185GA' is more upright than Draper, the fruit is rounder in shape and lighter blue color. New leaf growth of 'BB05-185GA' is reddish in color and fruit maturation is 6 weeks earlier than Draper.

'BB05-185GA' was created from a cross made in 2005 in a South Haven, Mich. greenhouse. Bushes were grown for one year in Grand Junction, Mich. and then planted in an observation trial near Manor, Ga. in 2006. The plant exhibited fruit and morphological characteristics that are desirable—maturity date, bush habit and vigor, and outstanding fruit quality. Additional plants have been propagated by softwood cuttings and tissue culture, and several multi-bush trials were established in 2011 throughout southeastern Georgia.

'BB05-185GA' was first asexually propagated by softwood cuttings that have been taken several times, the first in 2006. The propagated plants have retained the original characteristics. The variety roots readily from softwood cuttings or tissue culture microshoots.

All field observations were made in Spring 2012 on a 3-year old plant located in a trial near Manor, Ga., propagated from the original bush selection. Laboratory analysis of fruit characteristics were done in Grand Junction, Mich.

General comments: 'BB05-185GA' is a new and distinct low chill tetraploid Southern highbush blueberry (*Vaccinium*) variety of complex ancestry, based largely on *V. corymbosum* and with over 13% *V. darrowii* and small contributions of *V. angustifolium, V. tenellum*, and *V. ashei*. It is a productive mid-late season variety that ripens between Star, a widely planted mid-season highbush variety, and Climax, an early season rabbiteye variety. It is characterized as having a very large fruit with a very small and dry picking scar, light blue color, very firm with outstanding fruit quality and flavor for fresh market. The variety appears to be a good candidate for mechanical harvest due to a concentrated ripening period, upright bush habit, and easy detachment of firm fruit. It is intended for areas which successfully grow lower chill Southern highbush varieties. The fruit are large, typically 2 grams or more per berry, well exposed on a very upright bush with a small crown. The mean date of 50% flowering is March 1 in Southeast Georgia. Winter chill requirement for successful flowering and leafing is approximately 500 hours (<7° C.). Flowering and leafing are synchronous and during milder winters this variety tends to be evergreen. The fruit are large in size. The 50% ripening date is normally May 8. Fruit shape is oblate in shape with medium high amounts of waxy bloom that is mostly persistent after handling. This variety has outstanding flavor with very high levels of sweetness balanced with medium acidity and is also very firm and juicy. Storage ability in refrigeration can be 2 to 3 weeks. Thus, in part 'BB05-185GA' provides outstanding fruit quality and flavor, its harvest season fills a void between highbush and rabbiteye seasons and it has good machine harvest potential.

References to color refer to The Pantone Book of Color, Eisemann and Herbert, Harry N. Abrams, Inc. Publishers, New York, ISBN 0-8109-3711-5, 1990.

No spectrographic device was used to take color readings.

Morphological characteristics reference: Plant Systematics, Jones and Luchsinger, 2 Ed., McGraw Hill, New York, ISBN 0-07-032796-3, 1986.

Average size information:

*General description*.—Medium large bush, medium upright shape, 3-year plant 120 cm height, 70 cm width, height/width ratio 1.7:1.

*Growth*.—Very good.

*Productivity*.—Very good.

*Cold hardiness*.—Leaf and flower buds −5° C., open flowers and fruit −2° C.

Specific features of the variety:

Plant:

*Growth habit*.—Upright.

*Plant width*.—70 cm.

*Plant height*.—120 cm.

*Spread*.—70 cm.

*Productivity*.—5-6 lbs per mature bush.

*Cold hardiness/tolerance*.—Leaf and flower buds −5° C., flowers and fruit −2° C.

*Chilling requirement*.—500 hours below 7° C.

*Canes*.—Modestly branched, 6-8 canes/bush, 40-50 cm range, average 44 cm; medium number of laterals. Mature cane color — Pantone Adobe 17-1340. Texture — rough.

*Fruiting wood*.—Smooth, immature winter color — Pantone Barn Red 18-1531; immature summer color — Pantone Cedar 16-0526.

*Internode length range*.—12-20 mm range, average 16 mm.

*Surface texture of new wood*.—Smooth.

*Mature canes*.—Circular, 13 mm width.

*Time of beginning of leaf bud burst* (*include location(s)*).—February 20 (Manor, Ga.).

*Time of beginning of flowering* (*include location(s)*).—February 25 (Manor, Ga.).

*Time of fruit ripening* (*include location(s)*).—May 8 (Manor, Ga.).

*Disease resistance/susceptibility*.—None claimed.

Foliage:

*Leaf color*.—Upper — Pantone Avacado 18-0430; lower — Pantone Grasshopper 18-0332.

*Leaf arrangement*.—Alternate.

*Leaf margins*.—Entire.

*Leaf venation*.—Pinnate.

*Leaf apices*.—Acute.

*Leaf bases*.—Acute.

*Vein and petiole colouration*.—Pantone Cedar 16-0526.

*Petiole length*.—4 mm.

*Leaf dimensions*.—Overall shape: 55 mm-68 mm range, average 60 mm. Width: 22 mm-28 mm range, average 25 mm.

*Leaf margins*.—Entire; no visible pubescence or nectaries.

*Leaf surface*.—Smooth, upper and lower, no visible pubescence.

Flower:

*Flower shape*.—Urceolate.

*Flower bud number*.—Medium high.

*Flowers per cluster*.—8.

*Flower fragrance*.—Floral (like Gardenia).

*Corolla color*.—Pantone Snow White 11-1602.

*Corolla length*.—7 mm.

*Corolla aperture width*.—8 mm.

*Flower peduncle*.—5 mm.

*Color*.—Pantone Mellow Green 12-0426.

*Flower pedicel*.—7 mm.

*Color*.—Pantone Sage 16-0421.

*Calyx* (*with sepals*).—2 mm.

*Color*.—Pantone Sage 16-0421.

*Stamen*.—Length: 8 mm.

*Number per flower*.—10.

*Filament color*.—Pantone Coral Gold 16-1337.

*Style*.—9 mm, top of ovary to stigma tip.

*Color*.—Pantone Raffia 13-0725.

*Pistil*.—7 mm.

*Ovary color*.—Pantone Raffia 13-0725.

*Anther*.—Length: 3 mm.

*Number*.—10.

*Color*.—Pantone Coral Gold 16-1337.

*Pollen*.—Abundance: Fair to good. Color: Pantone Autumn Blonde 12-0813.

Fruit:

*Date of 50% maturity*.—May 8 (2012) (Manor, Ga.).

*Yield*.—5-6 lbs/bush.

*Berry color*.—With wax: Pantone Celestial Blue 13-4308. With wax removed: Pantone Midnight 19-4127.

*Berry flesh color*.—Pantone Frozen Dew 13-0513.

*Berry surface wax abundance*.—Medium-heavy, persistent.

*Calyx*.—Width — 8 mm; depth — 2 mm; shape — 5 lobed; slight ridging of lobes, turned inward.

*Berry weight*.—2.1 grams/berry.

*Berry size diameter*.—17 mm width, 14 mm height, Aspect (H/W) — 0.8.

*Berry shape*.—Oblate.

*Cluster density*.—Medium tight.

*Detachment force*.—Easy.

*Self-fruitfulness*.—Fair; will need cross pollination for maximum yield, earliness, and size.

*Fruit stem scar*.—1 mm, very small and dry.

*Berry firmness*.—Firm.

*Berry sweetness*.—Medium, high Brix° 11.2.

*Berry acidity*.—Medium, TA — 0.41.

*Berry flavor and texture*.—Outstanding with balanced sweetness and acidity, crunchy and juicy.

*Suitability for mechanical harvesting*.—Very possible due to firm fruit, bush shape, crown size, and concentration of ripening.

Seed:

*Seed abundance in fruit*.—Medium low.

*Seed color*.—Pantone Paprika 17-1553.

*Seed dry weight*.—NA.

*Seed size*.—1.5 mm.

Possible typical market uses: Fresh market, processing into jams, puree, yogurt.

Storage quality: Medium, 2-3 weeks in refrigerated storage. In addition, new shoots and leaves, especially in cool weather, typically have a distinct and rather persistent reddish tinge that changes to green as the foliage ages and weather warms.

What is claimed is:

1. A new and distinct cultivar of Blueberry plant named 'BB05-185GA' as described and shown herein.

* * * * *